US009717702B2

(12) United States Patent
Chandraratna (10) Patent No.: US 9,717,702 B2
(45) Date of Patent: Aug. 1, 2017

(54) TREATMENT OF CANCER WITH SPECIFIC RXR AGONISTS (71) Applicant: IO Therapeutics, Inc., San Juan Capistrano, CA (US)

(72) Inventor: Roshantha A. Chandraratna, Laguna Hills, CA (US)

(73) Assignee: IO Therapeutics, Inc., Santa Ana, CA (US)

( * ) Notice: Subject to any disclaimer, the term of this patent is extended or adjusted under 35 U.S.C. 154(b) by 0 days.

(21) Appl. No.: 14/994,031

(22) Filed: Jan. 12, 2016

(65) Prior Publication Data

US 2016/0120827 A1 May 5, 2016

Related U.S. Application Data (60) Continuation of application No. 13/323,510, filed on Dec. 12, 2011, now Pat. No. 9,308,186, which is a division of application No. 12/079,938, filed on Mar. 28, 2008, now Pat. No. 8,101,662, which is a continuation-in-part of application No. PCT/US2006/038252, filed on Oct. 2, 2006.

(60) Provisional application No. 60/722,264, filed on Sep. 30, 2005.

(51) Int. Cl.
*A61K 31/192* (2006.01)
*A61K 45/06* (2006.01)
*A61K 31/282* (2006.01)
*A61K 31/337* (2006.01)
*C12Q 1/68* (2006.01)

(52) U.S. Cl.
CPC .......... *A61K 31/192* (2013.01); *A61K 31/282* (2013.01); *A61K 31/337* (2013.01); *A61K 45/06* (2013.01); *C12Q 1/6886* (2013.01); *C12Q 2600/158* (2013.01)

(58) Field of Classification Search
CPC .............................. A61K 31/192; A61K 45/06
See application file for complete search history.

(56) References Cited

U.S. PATENT DOCUMENTS

| | | | |
|---|---|---|---|
| 5,466,861 A | 11/1995 | Dawson et al. | |
| 5,663,367 A | 9/1997 | Vuligonda et al. | |
| 5,675,033 A | 10/1997 | Vuligonda et al. | |
| 5,728,846 A | 3/1998 | Vuligonda et al. | |
| 5,739,338 A | 4/1998 | Beard et al. | |
| 5,763,635 A | 6/1998 | Vuligonda et al. | |
| 5,773,594 A | 6/1998 | Johnson et al. | |
| 5,776,699 A | 7/1998 | Klein et al. | |
| 5,780,647 A | 7/1998 | Vuligonda et al. | |
| 5,817,836 A | 10/1998 | Vuligonda et al. | |
| 5,877,207 A | 3/1999 | Klein et al. | |
| 5,917,082 A | 6/1999 | Vuligonda et al. | |
| 5,919,970 A | 7/1999 | Song et al. | |
| 5,952,345 A | 9/1999 | Klein et al. | |
| 5,958,954 A | 9/1999 | Klein et al. | |
| 5,998,655 A | 12/1999 | Vuligonda et al. | |
| 6,008,204 A | 12/1999 | Klein et al. | |
| 6,034,242 A | 3/2000 | Vuligonda et al. | |
| 6,037,488 A | 3/2000 | Song et al. | |
| 6,043,381 A | 3/2000 | Vuligonda et al. | |
| 6,048,873 A | 4/2000 | Vuligonda et al. | |
| 6,087,505 A | 7/2000 | Vuligonda et al. | |
| 6,090,810 A | 7/2000 | Klein et al. | |
| 6,114,533 A | 9/2000 | Vuligonda et al. | |
| 6,117,987 A | 9/2000 | Johnson et al. | |
| 6,147,224 A | 11/2000 | Vuligonda et al. | |
| 6,211,385 B1 | 4/2001 | Vuligonda et al. | |
| 6,218,128 B1 | 4/2001 | Klein et al. | |
| 6,225,494 B1 | 5/2001 | Song et al. | |
| 6,228,848 B1 | 5/2001 | Klein et al. | |
| 6,235,923 B1 | 5/2001 | Song et al. | |
| 6,313,163 B1 * | 11/2001 | Vuligonda ............. | A61K 31/20 514/311 |
| 6,313,168 B1 | 11/2001 | Pacifici et al. | |
| 6,403,638 B1 | 6/2002 | Vuligonda et al. | |
| 6,521,624 B1 | 2/2003 | Klein et al. | |
| 6,521,641 B1 | 2/2003 | Klein et al. | |
| 6,538,149 B1 | 3/2003 | Vuligonda et al. | |
| 6,555,690 B2 | 4/2003 | Johnson et al. | |
| 6,653,483 B1 | 11/2003 | Johnson et al. | |
| 6,720,423 B2 | 4/2004 | Vasudevan et al. | |
| 6,720,425 B2 | 4/2004 | Johnson et al. | |
| 6,818,775 B2 | 11/2004 | Johnson et al. | |
| 6,942,980 B1 | 9/2005 | Klein et al. | |
| 7,105,566 B2 | 9/2006 | Chandraratna et al. | |
| 7,166,726 B2 | 1/2007 | Vuligonda et al. | |
| 2002/0156054 A1 | 10/2002 | Klein et al. | |
| 2002/0173631 A1 | 11/2002 | Johnson et al. | |
| 2002/0193403 A1 | 12/2002 | Yuan et al. | |
| 2003/0013766 A1 | 1/2003 | Lamph et al. | |
| 2003/0219832 A1 | 11/2003 | Klein et al. | |
| 2004/0037025 A1 | 11/2004 | Murray et al. | |
| 2005/0171151 A1 | 8/2005 | Yuan et al. | |
| 2007/0054882 A1 | 3/2007 | Klein et al. | |
| 2007/0185055 A1 | 8/2007 | Jiang et al. | |
| 2007/0265449 A1 | 11/2007 | Vuligonda et al. | |

FOREIGN PATENT DOCUMENTS

WO 94/12880 A2 6/1994
WO 94/14777 7/1994

(Continued)

OTHER PUBLICATIONS

Golub et al., Science, vol. 286, Oct. 15, 1999, pp. 531-537.*
Balasubramanian et al. Carcinogenesis, 2004, vol. 25, No. 8, pp. 1377-1385.*
International Search Report for PCT/US2007/011730 mailed May 2, 2008.

(Continued)

*Primary Examiner* — Samira Jean-Louis
(74) *Attorney, Agent, or Firm* — K&L Gates LLP; Louis C. Cullman; Michelle Glasky Bergman (57) ABSTRACT

A method of treating cancer is disclosed comprising administering to a patient in need of such treatment a RXR agonist at a level below the RAR activating threshold and at or above the RXR effective dose.

10 Claims, 3 Drawing Sheets

(56) References Cited

FOREIGN PATENT DOCUMENTS

| WO | 96/39374 A1 | 12/1996 |
|---|---|---|
| WO | 97/09297 | 3/1997 |
| WO | 99/33821 | 7/1999 |
| WO | 99/63980 A1 | 12/1999 |
| WO | 00/20370 A1 | 4/2000 |
| WO | 01/07028 A2 | 2/2001 |
| WO | 02/089781 | 11/2002 |
| WO | 02/089842 | 11/2002 |
| WO | 03/062369 | 7/2003 |
| WO | 03/078567 | 9/2003 |
| WO | 03/093257 A1 | 11/2003 |
| WO | 03/101928 | 12/2003 |
| WO | 2004/046096 | 6/2004 |

OTHER PUBLICATIONS

Johnson, A. et al., Synthesis and biological activity of high-affinity retinoic acid receptor antagonists. Bioorganic & Medicinal Chemistry, vol. 7, No. 7, pp. 1321-1338, Elsevier Science Ltd., Jul. 1999.

Klein et al., Identification and functional separation of retinoic acid receptor neutral antagonists and inverse agonists. The Journal of Biological Chemistry, vol. 271, No. 37, pp. 22692-22696, 1996.

Mangelsdorf et al., Characterization of three RXR genes that mediate the action of 9-cis retinoic acid. Genes and Development 6:329-344, 1992.

Teng, M. et al., Identification of highly potent retinoic acid receptor alpha-selective antagonists. Journal of Medicinal Chemistry, vol. 40, pp. 2445-2451, 1997.

Walkley, C.R. et al., Retinoic acid receptor antagonism in vivo expands the numbers of precursor cells during granulopoiesis. Leukemia, vol. 16, No. 9, pp. 1763-1772, Nature, Sep. 2002.

Liu et al. "Combination therapy of insulin-like growth factor binding protein-3 and retinoid X receptor ligands synergize on prostate cancer apoptosis in vitro and in vivo." Clin Cancer Res 11:4851-4856, 2005.

Macchia et al. "RXR receptor agonist suppression of thyroid function: central effects in the absence of thyroid hormone receptor." Am J Physiol Endocrinol Metab 283:E326-E331, 2002.

Cal et al. "Doxazosin: a new cytotoxic agent for prostate cancer?" BJU Int. 85:672-675, 2000.

Lampen et al. "Effects of receptor-selective retinoids on CYP26 gene expression and metabolism of all-trans-retinoic acid in intestinal cells." Drug Metab Dispos 29:742-747, 2001.

Blumenschein et al. "A randomized phase III trial comparing bexarotene/carboplatin/paclitaxel versus carboplatin/paclitaxel in chemotherapy-naive patients with advanced or metastatic non-small cell lung cancer (NSCLC)." ASCO 2007 Annual Meeting Abstract 7001.

Jassem et al. "A randomized phase III trial comparing bexarotene/cisplatin/vinorelbine versus cisplatin/vinorelbine in chemotherapy-naive patients with advanced or metastatic non-small cell lung cancer (NSCLC)." ASCO 2005 Annual Meeting Abstract 7024.

Govindan et al. "Phase II trial of bexarotene capsules in patients with non-small cell lung cancer (NSCLC) who have failed at least 2 prior system therapies for stage IIIB/IV disease." ASCO 2005 Annual Meeting Abstract 7116.

Petty et al. "Weekly paclitaxel (Taxol(R)), carboplatin (Paraplatin(R)), and bexarotene (Targretin(R)) for the treatment of patients with advanced non-small cell lung cancer: efficacy results from a Phase I/II study." ASCO 2005 Annual Meeting Abstract 7243.

Bordoni et al. "Bexarotene improves TTP in untreated, advanced NSCLC when given in combination with carboplatin/paclitaxel," ASCO 2005 Annual Meeting Abstract 7270.

Estephan et al. "Phase II trial of gemcitabine (G), carboplatin (C) and bexarotene (B) in patients (pts.) with newly diagnosed, locally-advanced or metastatic non-small cell carcinoma of the lung." ASCO 2005 Annual Meeting Abstract 7308.

Miller et al. "Initial clinical trial of a selective retinoid X receptor ligand LGD1069." J Clin Oncol 15:790-795, 1997.

Rigas et al. "Emerging role of rexinoids in non-small cell lung cancer: Focus on bexarotene," The Oncologist 10:22-33, 2005.

Suh et al. "Prevention and treatment of experimental breast cancer with the combination of a new selective estrogen receptor modulator, arzoxifene, and a new rexinoid LG100268." Clin Cancer Res 8:3270-3275, 2002.

* cited by examiner

TREATMENT OF CANCER WITH SPECIFIC RXR AGONISTS

CROSS REFERENCE TO RELATED APPLICATIONS

The present application is a continuation of U.S. patent application Ser. No. 13/323,510 filed Dec. 12, 2011, which is a divisional of U.S. patent application Ser. No. 12/079,938 field Mar. 28, 2008 and now U.S. Pat. No. 8,101,662, which is a continuation-in-part of International Application PCT/US2006/038252 filed Oct. 2, 2006, which claims the benefit of U.S. Provisional Patent Application 60/722,264 filed Sep. 30, 2005. The contents of each of these applications are incorporated by reference herein in their entirety.

BACKGROUND

Compounds which have retinoid-like biological activity are well known in the art and are described in numerous United States patents including, but not limited to, U.S. Pat. Nos. 5,466,861; 5,675,033 and 5,917,082, all of which are herein incorporated by reference. Preclinical studies with rexinoids suggest that selective activation of retinoid X receptors (RXR), which modulate functions associated with differentiation, inhibition of cell growth, apoptosis and metastasis, may be useful in treating a variety of diseases associated with the biochemical functions modulated by RXR.

For example, TARGRETIN® (bexarotene), which is a RXR agonist with RAR agonist activity as well, was approved by the U.S. Food and Drug Administration for the treatment, both oral and topical, of cutaneous manifestations of cutaneous T-cell lymphoma in patients who are refractory to at least one prior systemic therapy. Further, recent clinical studies that were conducted using TARGRETIN® suggest that there is potential for RXR agonists in the treatment of non-small cell lung cancer (NSCLC). Encouraging results were obtained with TARGRETIN® in several Phase II studies in NSCLC. However, the pivotal Phase III clinical study did not show increased survival. Therefore, there is a need for new technologies that increase the efficacy of RXR agonists when used to treat solid tumors such as NSCLC.

SUMMARY

It is now proposed that activation of RAR by RXR agonists decreases the efficacy of the RXR agonists as anti-cancer agents. As such, the efficacy of treatment of cancer patients with RXR agonists can be improved by administering the drug at a dose which activates RXR but which activates RAR minimally or not all. Based on this proposal, novel methods of treating a patient with cancer are disclosed herein.

The present invention provides a method of treating cancer comprising administering to a patient in need of such treatment a RXR agonist at a level below the RAR activating threshold and at or above the RXR effective dose.

In another embodiment, the present invention provides a method of treating cancer comprising dosing a patient in need of such treatment with increasing concentrations of a RXR agonist to determine the RAR activating threshold and the RXR effective dose for the patient; and administering to the patient the RXR agonist at a level below the RAR activating threshold and at or above the RXR effective dose.

In yet another embodiment, the present invention provides a method for treating cancer comprising the step of administering to a patient in need of such treatment an effective amount of a RXR agonist having a therapeutically beneficial mean RXR $EC_{90}$:RAR $EC_{10}$ ratio range. A therapeutically beneficial mean RXR $EC_{90}$:RAR $EC_{10}$ ratio is at least about 40. Alternatively, a therapeutically beneficial mean RXR $EC_{90}$:RAR $EC_{10}$ ratio is at least about 100. In another alternative, a therapeutically beneficial mean RXR $EC_{90}$:RAR $EC_{10}$ ratio is at least about 200.

BRIEF DESCRIPTION OF THE DRAWING

FIGS. 1A-1D illustrate the effects of VTP 194204 on nude mice xenografted with human H292 NSCLC tumors. Nude mice were randomized into 4 groups of 10 animals each based on body weight and xenografted subcutaneously in the right flank with H292 cells ($2\times10^6$ cells). Drug treatment was started immediately after xenografting and continued for 35 days (5 animals of each group) or 55 days (remaining 5 animals). The animals were treated with vehicle (VEH), TAXOL®5 mg/kg/week, once a week, i.p., VTP 194204 10 mg/kg/day, 5 days a week, by oral gavage, or VTP 194204+TAXOL®. Tumor sizes were measured periodically for 35 days (FIG. 1A). Animals #1-5 of each group were sacrificed after 35 days of treatment and gastrocnemus muscles were determined (FIG. 1O). The body weights and overall appearance of animals #6 through #10 from each group were followed for an extended period (FIG. 1B and FIG. 1D). To appropriately show the overall health of these animals, pictures were taken from their tumor-free left flank on day 55 (FIG. 1D).

DETAILED DESCRIPTION

To maximize efficacy, anticancer agents are most commonly administered at or near to the maximum tolerated dose (MTD). It is now proposed that certain RXR agents can not only be efficaciously administered at doses significantly lower than MTD, but are actually more effective at these lower doses than at or near the MTD. As such, the efficacy of the treatment can be enhanced while lowering side effects. Examples of suitable doses include: between about 0.1 to about 10 $mg/m^2$/day; between about 0.5 to about 2 $mg/m^2$/day; between about 0.01-100 $mg/m^2$/day; between about 1 to about 50 $mg/m^2$/day; between about 0.1 $mg/m^2$/day to about 1.0 $mg/m^2$/day; between about 1.0 $mg/m^2$/day and about 5.0 $mg/m^2$/day; between about 5.0 $mg/m^2$/day and about 10.0 $mg/m^2$/day; between about 10.0 $mg/m^2$/day and about 15 $mg/m^2$/day; between about 15.0 $mg/m^2$/day and about 20.0 $mg/m^2$/day; between about 20.0 $mg/m^2$/day and about 25.0 $mg/m^2$/day; between about 30.0 $mg/m^2$/day and about 35.0 $mg/m^2$/day; between about 35.0 $mg/m^2$/day and about 40.0 $mg/m^2$/day; between about 40.0 $mg/m^2$/day and about 45.0 $mg/m^2$/day; between about 45.0 $mg/m^2$/day and about 50.0 $mg/m^2$/day; between about 50.0 $mg/m^2$/day and about 55.0 $mg/m^2$/day; between about 55.0 and about 60.0 $mg/m^2$/day; between about 60.0 $mg/m^2$/day and about 65.0 $mg/m^2$/day; between about 65.0 $mg/m^2$/day and about 70.0 $mg/m^2$/day; between about 70.0 $mg/m^2$/day and about 75.0 $mg/m^2$/day; between about 75.0 $mg/m^2$/day and about 80.0 $mg/m^2$/day; between about 80.0 $mg/m^2$/day and about 85.0 $mg/m^2$/day; between about 85.0 and about 90.0 $mg/m^2$/day; between about 85.0 $mg/m^2$/day and about 90.0 $mg/m^2$/day; between about 90.0 $mg/m^2$/day and about 95.0 $mg/m^2$/day; and between about 95.0 $mg/m^2$/day and about 100.0 $mg/m^2$/day.

DEFINITIONS

CYP26 means Cytochrome P450 Type 26.

CRBPI means Cellular Retinol Binding Protein.

The RXR agonists can optionally be administered in the disclosed methods in combination with a second anti-cancer agent. Suitable anti-cancer agents include cytotoxic drugs, including, but not limited to, TAXOL® (paclitaxel), TAXOTERE® (docetaxel), and the like and mixtures thereof. Additional anti-cancer agents include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin 11 (including recombinant interleukin 11, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Platinum based drugs include, but are not limited to, carboplatin, cisplatin, and the like and mixtures thereof.

RAR means one or more of RAR α, β and γ.

RXR means one or more of RXR α, β and γ.

A RAR biomarker is a distinctive biological, biochemical or biologically derived indicator that signifies patient RAR activity. RAR biomarkers include, but are not limited to, CYP26 levels, CRBPI levels and the like and combinations thereof.

RAR activation threshold means one or more of the following: a CYP26 level of a 2-fold increase over baseline, and a CRBPI level of a 2-fold increase over baseline.

RXR $EC_{90}$:RAR $EC_{10}$ ratio is calculated by taking the inverse of the RXR $EC_{90}$ α, β and γ values (nM) divided by the corresponding inverse of the RAR $EC_{10}$ α, β and γ values (nM). For example, the RXR $EC_{90}$:RAR $EC_{10}$ ratio is determined by dividing RAR $EC_{10}$ by RXR $EC_{90}$ for α, β and γ. Thus, a value is obtained for all three receptors, referred to herein as (RXR $EC_{90}$:RAR $EC_{10}$ ratio)$_α$, (RXR $EC_{90}$:RAR $EC_{10}$ ratio)$_β$ and (RXR $EC_{90}$:RAR $EC_{10}$ ratio)$_γ$ for α β and γ, respectively. For example, (RXR $EC_{90}$:RAR $EC_{10}$ ratio), is determined by dividing RAR $EC_{10}$α by RXRα $EC_{90}$. The mean RXR $EC_{90}$:RAR $EC_{10}$ ratio is the average of all three values. An example is provided below in Tables 1A and 1B.

TABLE 1(A)

Comparison of safety margins of VTP 194204 and TARGRETIN ®. RXR $EC_{90}$ and RAR $EC_{10}$ values of VTP 194204 and TARGRETIN ®.

| Compound | RXR $EC_{90}$ (nM) | | | RAR $EC_{10}$ (nM) | | |
|---|---|---|---|---|---|---|
| | α | β | γ | α | β | γ |
| VTP 194204 | 0.1 | 1 | 0.1 | 300 | 200 | 200 |
| TARGRETIN ® | 15 | 100 | 15 | 1000 | 200 | 300 |

TABLE 1(B)

Comparison of safety margins of VTP 194204 and TARGRETIN ®. Ratio of RXR EC90 to RAR EC10 for VTP 194204 and TARGRETIN ®.

| | RXR $EC_{90}$:RAR $EC_{10}$ ratio | | | |
|---|---|---|---|---|
| Compound | α | β | γ | Mean |
| VTP 194204 | 3000 | 200 | 2000 | 1730 |
| TARGRETIN ® | 67 | 2 | 20 | 30 |

Table 1

RXR effective dose means the dose needed to fully activate RXRs as ascertained by pharmacodynamic markers (RXR biomarkers) such as reductions in TSH levels.

Representative examples of RXR agonists for use herein and processes for their preparation are well known in the art, e.g., in U.S. Pat. Nos. 5,663,367; 5,675,033; 5,780,647; 5,817,836; 5,917,082; 6,034,242; 6,048,873; 6,114,533; 6,147,224; 6,313,163; 6,403,638 and 6,720,423, the contents of each of which are incorporated by reference herein in their entirety. Many of the following compounds are included in one or more of these applications.

A class of compounds for use herein is represented by Formula I:

(I)

wherein Z is a radical shown in Formula II, (II)

Y is selected from thienyl and furyl, the groups being optionally with one or two $R_4$ groups, the divalent Y radical being substituted by the Z and —($CR_1$=$CR_1$—$CR_1$=$CR_1$)— groups on adjacent carbons; n is 1 or 2; $R_1$ and $R_2$ independently are H, lower alkyl or fluoroalkyl; $R_3$ is hydrogen, lower alkyl, Cl or Br; $R_4$ is lower alkyl, fluoroalkyl or halogen, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, $OCOR_7$, $CR_7(OR_{12})_2$, $CR_7OR_{13}O$, or tri-lower alkylsilyl, where $R_7$ is an alkyl, cycloalkyl or alkenyl group, containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ carbons, or a cycloalkyl groups of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

Another class of compounds for use herein is represented by Formula III:

wherein $R_2$ is hydrogen or lower alkyl; $R_3$ is hydrogen or lower alkyl, and B is hydrogen, COOH or a pharmaceutically acceptable salt thereof, $COOR_8$, $CONR_9R_{10}$, —CHOH, $CHOR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

Another class of compounds for use herein is represented by Formula IV:

wherein n is 1 or 2; $R_1$ and $R_2$ independently are H, lower alkyl or fluoroalkyl; $R_3$ is hydrogen, lower alkyl, Cl or Br; $R_4$ is H, lower alkyl, fluoroalkyl or halogen, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl where $R_7$ is an alkyl, cycloalkyl or alkenyl group containing 1 to 5 carbons, $R_8$ is an alkyl group of 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

Another class of compounds for use herein is represented by Formula V:

where $R_4$ is lower alkyl of 1 to 6 carbons; B is COOH or $COOR_8$ where $R_8$ is lower alkyl of 1 to 6 carbons, and the configuration about the cyclopropane ring is cis, and the configuration about the double bonds in the pentadienoic acid or ester chain attached to the cyclopropane ring is trains in each of the double bonds, or a pharmaceutically acceptable salt of the compound.

Another class of compounds for use herein is represented by Formula VI:

wherein Z is a radical shown in Formula VII:

Y is cycloalkyl or cycloalkenyl of 3 to 8 carbons optionally substituted with one or two $R_4$ groups, or Y is selected from phenyl, pyridyl, thienyl, furyl, pyrrolyl, pyridazinyl, pyrimidiyl, pyrazinyl, thiazolyl, oxazolyl, and imidazolyl, the groups being optionally substituted with one or two $R_4$ groups, the divalent Y radical being substituted by the Z and —$CR_1$=$CR_1$—$CR_1$=$CR_1$)— groups on adjacent carbons; X is S or O; $R_1$ and $R_2$ independently are H, lower alkyl or fluoroalkyl; $R_3$ is hydrogen, lower alkyl, Cl or Br; $R_4$ is lower alkyl fluoroalkyl or halogen, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

Another class of compounds for use herein is represented by Formula VIII:

(VIII)

wherein X is S or O; $R_2$ is hydrogen or lower alkyl; $R_3$ is hydrogen or lower alkyl, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

Another class of compounds for use herein is represented by Formula IX:

wherein Z is selected from the group consisting of the radicals a radical shown in Formulae X and XI:

(X)

(XI)

Y is selected from pyridyl, pyrrolyl, pyridazinyl, pyrimidinyl, pyrazinyl, thiazolyl, oxazolyl, and imidazolyl, the groups being optionally substituted with one or two $R_4$ groups, the divalent Y radical being substituted by the Z and —$CR_1$=$CR_1$—$CR_1$=$CR_1$)— groups on adjacent carbons; X is $NR_5$; n is 1 or 2; $R_1$ and $R_2$ independently are H, lower alkyl or fluoroalkyl; $R_3$ is hydrogen, lower alkyl, Cl or Br; $R_4$ is lower alkyl, fluoroalkyl or halogen; $R_5$ is H or lower alkyl, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_2)_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2 to 5 carbons.

Another compound for use herein is enantiomerically substantially pure compound of Formula XII:

(XII)

wherein R is H, lower alkyl or 1 to 6 carbons, or a pharmaceutically acceptable salt of the compound.

Another class of compounds for use herein is represented by Formula XIII:

(XIII)

wherein Z is the group shown in Formula XIV:

(XIV)

Y is cyclopropyl, the Y group being optionally substituted with one or two $R_4$ groups, the divalent Y radical being substituted by the Z and —$(CR_1$=$CR_1$—$CR_1$=$CR_1$)— groups on adjacent carbons; X is $NR_5$; $R_1$ and $R_2$ independently are H, lower alkyl or fluoroalyl; $R_3$ is hydrogen, lower alkyl, Cl or Br; $R_4$ is lower alkyl, fluoroalkyl or hydrogen; $R_5$ is H or lower alkyl, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2 to 5 carbons.

Another class of compounds for use herein is represented by Formula XV:

(XV)

wherein X is $NR_5$; $R_5$ is H or lower alkyl; $R_2$ is H or lower alkyl; $R_3$ is H or lower alkyl, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and R.sub.$_{13}$ is divalent alkyl radical of 2 to 5 carbons.

Another class of compounds for use herein is represented by Formula XVI:

(XVI)

where Y is a bivalent radical having Formula XVII (XVII)

the two $X_1$ groups jointly represent an oxo (=O) or thione (=S) function, or $X_1$ is independently selected from H or alkyl of 1 to 6 carbons; the two $X_2$ groups jointly represent an oxo (=O) or a thione (=S) function, or $X_2$ independently selected from H or alkyl of 1 to 6 carbons, with the proviso that one of the joint $X_1$ grouping or of the joint $X_2$ grouping represents an oxo (=O) or thione (=S) function; W is O, $C(R_1)_2$, or W does not exist; $R_1$ is independently H, lower alkyl of 1 to 6 carbons, or lower fluoroalkyl of 1 to 6 carbons; $R_2$ is independently H, lower alkyl of 1 to 6 carbons, or lower fluoroalkyl of 1 to 6 carbons; $R_3$ is hydrogen, lower alkyl of 1 to 6 carbons, $OR_1$, fluoro substituted lower alkyl of 1 to 6 carbons halogen, $NO_2$, $NH_2$, $NHCO(C_1-C_6$ alkyl), or $NHCO(C_1-C_6)$ alkenyl; A is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CH(OR_{13}O)$, —$COR_7$, $CR_7(OR_{12})_2$, $CR_7(OR_{13}O)$, or $Si(C_1\text{-6alkyl})_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkyphenyl, $R_9$ and $R_{10}$ independently are hydrogen, an alkyl group of 1 to 10 carbons, or a cycloalkyl group of 5-10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2 to 5 carbons, and $R_{14}$ is H, alkyl of 1 to 10 carbons, fluoro-substituted alkyl of 1 to 10 carbons, alkenyl of 2 to 10 carbons and having 1 to 3 double bonds.

Another class of compounds for use herein is represented by Formula XVIII:

(XVIII)

wherein $R_1$ is independently H, lower alkyl of 1 to 6 carbons, or lower fluoroalkyl of 1 to 6 carbons; $R_1^*$ is hydrogen or $C_{1\text{-}6}$-alkyl; $R_2^*$ is independently H, lower alkyl of 1 to 6 carbons, or lower fluoroalkyl of 1 to 6 carbons; $R_3^*$ is hydrogen, lower alkyl of 1 to 6 carbons, fluoro substituted lower alkyl of 1 to 6 carbons or halogen; $X_1^*$ is an oxo (=O) or a thione (=S) group; $A^*$ is hydrogen, COOH or a pharmaceutically acceptable salt thereof, $COOR_8$, $CONR_9R_{10}$, where $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl, hydroxyphenyl or lower alkylphenyl, and the cyclopropyl group is attached to the 6 or 7 position of the tetrahydroquinoline moiety, and $R_{14}^*$ is alkyl of 1 to 10 carbons or fluoro-substituted alkyl of 1 to 10 carbons.

Another class of compounds for use herein is represented by Formulae XIX, XX or XXI:

(XIX)

-continued where X is O, S, or $(CR_1R_1)_n$ where n is 0, 1 or 2; Y is a bivalent radical having Formulae XXII or XXIII where o is an integer between 1 through 4 or Y is a bivalent aryl or 5 or 6 membered heteroaryl radical having 1 to 3 heteroatoms selected from N, S and O, the aryl or heteroaryl groups being unsubstituted, or substituted with 1 to 3 $C_{1-6}$ alkyl or with 1 to 3 $C_{1-6}$ fluoroalkyl groups with the proviso that when the compound is in accordance with Formula 2 then Y is not a 5 or 6 membered ring; $X_1$ is S or $NH$; $R_1$ is independently H, lower alkyl of 1 to 6 carbons, or lower fluoroalkyl of 1 to 6 carbons; $R_2$ is independently H, lower alkyl of 1 to 6 carbons, $OR_1$, adamantly, or lower fluoroalkyl of 1 to 6 carbons, or the two $R_2$ groups jointly represent an oxo (=O) group with the proviso that when the compound is in accordance with Formula 2 then at least one of the $R_2$ substituents is branched-chain alkyl or adamantly; $R_3$ is hydrogen, lower alkyl of 1 to 6 carbons, $OR_1$, fluoro substituted lower alkyl of 1 to 6 carbons or halogen, $NO_2$, $NH_2$, $NHCO(C_1-C_6$ alkyl, or $NHCO(C_1-C_6)$ alkenyl; A is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CH(OR_{13}O)$, —$COR_7$, $CR_7(OR_{12})_2$, $CR_7(OR_{13}O)$, or $Si(C_{1-8}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl, hydroxyphenyl or lower alkylphenyl, $R_{12}$ is lower alkyl, and $R_{13}$ is divalent alkyl radical of 2-5 carbons, and $R_{14}$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, naphthyl-$C_1-C_{10}$alkyl, $C_1-C_{10}$-alkenylphenyl having 1 to 3 double bonds, $C_1-C_{10}$-alkynylphenyl having 1 to 3 triple bonds, phenyl-$C_1-C_{10}$alkenyl having 1 to 3 double bonds, phenyl-$C_1-C_{10}$alkenyl having 1 to 3 triple bonds, hydroxyl alkyl of 1 to 10 carbons, hydroxyalkenyl having 2 to 10 carbons and 1 to 3 double bonds, hydroxyalkynyl having 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds where the acyl group is represented by $COR_8$, or $R_{14}$ is a 5 or 6 membered heteroaryl group having 1 to 3 heteroatoms, the heteroatoms being selected from a group consisting of O, S, and N, the heteroaryl group being unsubstituted or substituted with a $C_1$ to $C_{10}$ alkyl group, with a $C_1$ to $C_{10}$ fluoroalkyl group, or with halogen, and the dashed line in Formula XXII represents a bond or absence of a bond.

Another class of compounds for use herein is represented by Formulae XXIV:

wherein R is H, lower alkyl of 1 to 6 carbons, or a pharmaceutically acceptable salt of the compound.

Another class of compounds for use herein is represented by Formulae XXV:

wherein R is H, lower alkyl of 1 to 6 carbons, and $R_1$ is iso-propyl or tertiary-butyl, or a pharmaceutically acceptable salt of the compound.

Another class of compounds for use herein is represented by Formulae XXVI:

wherein R is H, lower alkyl of 1 to 6 carbons, and $R_1$ is iso-propyl, n-butyl or tertiary-butyl, or a pharmaceutically acceptable salt of the compound.

Another class of compounds for use herein is represented by Formulae XXVII:

where X is O or S; Y is a bivalent cycloalkyl or cycloalkenyl radical optionally substituted with one to four $R_4$ groups, the cycloalkenyl radical having 5 to 6 carbons and one double bond, or Y is a bivalent aryl or 5 or 6 membered heteroaryl radical having 1 to 3 heteroatoms selected from N, S and O, the aryl or heteroaryl groups optionally substituted with 1 to 4 $R_4$ groups with the proviso that the cycloalkyl or the cycloalkenyl radical is not substituted on the same carbon with the condensed cyclic moiety and with the diene containing moiety; $R_1$ is independently H, alkyl of 1 to 6 carbons, or fluoroalkyl of 1 to 6 carbons; $R_2$ is independently H, alkyl of 1 to 8 carbons, or fluoroalkyl of 1 to 8 carbons; $R_{12}$ is independently H, alkyl of 1 to 8 carbons, or fluoroalyl of 1 to 8 carbons; $R_3$ is hydrogen, alkyl of 1 to 10 carbons, fluoro substituted alkyl of 1 to 10 carbons, halogen, alkoxy of 1 to 10 carbons, or alkylthio of 1 to 10 carbons; $NO_2$, $NH_2$, $NHCO(C_1-C_6$ alkyl, $NHCO(C_1-C_6)$ alkenyl, $NR_1H$ or $N(R_1)_2$, benzyloxy, $C_1-C_6$alkyl-substituted benzyloxy, or $R_3$ is selected from the groups shown below, $R_4$ is H, halogen, alkyl of 1 to 10 carbons, fluoro substituted alkyl of 1 to 6 carbons, alkoxy of 1 to 10 carbons, or alkylthio of 1 to 10 carbons; m is an integer having the values of 0 to 3; r is an integer having the values of 1 to 10; s is an integer having the values 1 to 4; t is an integer having the values 1 to 5;

represents a 5 or 6 membered heteroaryl ring having 1 to 3 heteroatoms selected from the group consisting of N, S and O; B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons, a cycloalkyl group of 5 to 10 carbons or trimethylsilylalkyl where the alkyl group has 1 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2 to 5 carbons.

Another class of compounds for use herein is represented by Formulae XXVIII:

(XXVIII)

wherein $R_1H$ or methyl; $R_8$ is H, alkyl of 1 to 6 carbons, or a pharmaceutically acceptable cation, and $R_3$ is hydrogen, alkyl of 1 to 10 carbons, halogen, alkoxy of 1 to 10 carbons, or $R_3$ is selected from the groups shown below where $R_4$ is H, halogen, alkyl of 1 to 10 carbons, carbons, alkoxy of 1 to 10; r is an integer having the values of 1 to 10; s is an integer having the values 1 to 4;

represents a 5 or 6 membered heteroaryl ring having 1 to 3 heteroatoms selected from the group consisting of N, S and O, and t is an integer having the values 1 to 5.

A preferred compound for use herein is VTP 194204 which means 3,7-dimethyl-6(S),7(S)-methano,7-[1,1,4,4-tetramethyl-1,2,3,4-tetrahydron-aphth-7-yl]2(E), 4(E) heptadienoic acid, and has the following chemical structure:

Pharmaceutically acceptable salts of RXR agonists can also be used in the disclosed method. Compounds disclosed herein which possess a sufficiently acidic, a sufficiently basic, or both functional groups, and accordingly can react with any of a number of organic or inorganic bases, and inorganic and organic acids, to form a salt.

Acids commonly employed to form acid addition salts from RXR agonists with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, di nitrobenzoate, hydroxybenzoate, methoxybenzoate, phthalate, sulfonate, xylenesulfonate, phenylacetate, phenylpropionate, phenyl butyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Bases commonly employed to form base addition salts from RXR agonists with acidic groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

TSH means thyroid stimulating hormone.

TSH modulating agents include, but are not limited to, rexinoids, thyroid hormones and the like and mixtures thereof.

The instant invention provides a method of treating cancer comprising administering to a patient in need of such treatment a RXR agonist at a level below the RAR activating threshold and at or above the RXR effective dose.

In another embodiment, the invention provides a method of treating cancer comprising dosing a patient in need of such treatment with increasing concentrations of a RXR agonist to determine the RAR activating threshold and the RXR effective dose for the patient; administering to the patient the RXR agonist at a level below the RAR activating threshold and at or above the RXR effective dose.

Examples of cancers which can be treated by the disclosed methods include Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer, Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor, Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor, Glioma, Childhood Brain Stem; Glioma, Childhood Visual pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver, Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy, Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer, Nasopharyngeal Cancer, Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer, Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer, Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual pathway and Hypothalamic Glioma, Childhood; Vulvar Cancer; Waldenstrom's Macroglobulinemia; and Wilms' Tumor. In a preferred embodiment, the cancer is non-small cell lung cancer, breast or prostate cancer.

In another preferred embodiment, the RXR effective dose can be determined by the reduction of the patient's thyroid stimulating hormone (TSH) levels.

In yet another preferred embodiment, the RAR activating threshold can be determined by measuring at least one RAR biomarkers expressed by the patient.

In still yet another preferred embodiment, the RAR biomarker is selected from the group consisting of CYP26 level, CRBPI level, and combinations thereof.

In yet another preferred embodiment, the invention further includes measuring the patient's $C_{max}$ of the RXR agonist and adjusting the dose to maintain the patient's $C_{max}$ at an optimal level.

In one embodiment, the RXR agonist is TARGRETIN®. In another embodiment, the RXR agonist is 3,7-dimethyl-6(S),7(S)-methano,7-[1,1,4,4-tetramethyl-1,2,3,4-tetrahydron-aphth-7-yl]2(E),4(E) heptadienoic acid.

If desired, the methods can further include treating the patient with at least one other anti-cancer agent. Preferred anti-cancer agents include, but are not limited to, a platinum-based compound, a cytotoxic drug and the like and mixtures thereof.

In a preferred embodiment, the method further includes treating the patient with one or more triglyceride lowering agents.

In a preferred embodiment, the method further includes treating the patient with one or more TSH modulating agents.

In another embodiment, the invention provides a method for treating cancer via modulation of RXR including at least the step of administering to a patient in need of such treatment an effective amount of a RXR agonist having a therapeutically beneficial RXR $EC_{90}$:RAR $EC_{10}$ ratio range. In a preferred embodiment, the mean of the RXR $EC_{90}$:RAR $EC_{10}$ ratio is at least about 40. In a more preferred embodiment, the mean of the RXR $EC_{90}$:RAR $EC_{10}$ ratio is at least about 200. Alternatively, the RXR $EC_{90}$:RAR $EC_{10}$ ratio for one of α, β and γ is at least about 40. More preferably, the RXR $EC_{90}$:RAR $EC_{10}$ ratio for one of α, β and γ are all at least about 200. Typically, the (RXR $EC_{90}$:RAR $EC_{10}$ ratio)▢ is at least 40, more typically at least 200. In another alternative, the RXR $EC_{90}$:RAR $EC_{10}$ ratio for α, β and γ are all at least about 40. More preferably, the RXR $EC_{90}$:RAR $EC_{10}$ ratio for α, β and γ are all at least about 200.

A "patient" is a mammal, preferably a human, but can also be an animal in need of veterinary treatment, e.g., companion animals (e.g., dogs, cats, and the like), farm animals (e.g., cows, sheep, pigs, horses, and the like) or laboratory animals (e.g., rats, mice, guinea pigs, and the like).

The RXR agonist compounds for use in the methods of the present invention may be used as is or incorporated into a pharmaceutical composition. All modes of administrations are contemplated, e.g., orally, rectally, parenterally, topically, or by intravenous, intramuscular, intrasternal or subcutaneous injection or in a form suitable by inhalation. The formulations may, where appropriate, be conveniently presented in discrete dosage units and may be prepared by any of the methods well known in the art of pharmacy. The compounds will ordinarily be formulated with one or more pharmaceutically acceptable ingredients in accordance with known and established practice. Thus, the pharmaceutical composition can be formulated as a liquid, powder, elixir, injectable solution, suspension, suppository, etc.

Formulations for oral use can be provided as tablets or hard capsules wherein the compounds are mixed with an inert solid diluent such as calcium carbonate, calcium phosphate or kaolin, or as soft gelatin capsules wherein the active ingredients are mixed with water or miscible solvents such as propylene glycol, PEGs and ethanol, or an oleaginous medium, e.g., peanut oil, liquid paraffin or olive oil.

For topical administration in the mouth, the pharmaceutical compositions can take the form of buccal or sublingual tablet, drops or lozenges formulated in conventional manner.

For topical administration to the epidermis, the compounds can be formulated as creams, gels, ointments or lotions or as transdermal patches. Such compositions can, for example, be formulated with an aqueous or oily base with the addition of suitable thickening, gelling, emulsifying, stabilizing, dispersing, suspending, and/or coloring agents.

The compounds can also be formulated as depot preparations. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example as a sparingly soluble salt.

The compounds can be formulated for parenteral administration by injection, conveniently intravenous, intramuscular or subcutaneous injection, for example by bolus injection or continuous intravenous infusion. Formulations for injection can be presented in unit dosage from, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the compounds may be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glyceride.

For intranasal administration, the compounds can be used, for example, as a liquid spray, as a powder or in the form of drops.

For administration by inhalation, the compounds can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit can be determined by providing a valve to deliver a metered amount. Capsules and cartridges of, e.g., gelatin for use in an inhaler or insulator can be formulated containing a powder mix of the retinoid compound and a suitable powder base such as lactose or starch.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl- or -n-propyl-p-hydroxy benzoate, one or more coloring agents, one or more flavoring agents and one or more sweetening agents, such as sucrose, saccharin or sodium or calcium cyclamate.

The compounds will be administered in an amount which is at a level below the RAR activating threshold and at or above the RXR effective dose in accordance with the invention. These amounts can be determined by one skilled in the art.

The following are non-limiting embodiments of the invention:

EXAMPLE 1

Prophetic Example

While not intending to be bound by any particular theory, one aspect of the instant invention contemplates that TARGRETIN®, particularly at high doses, activates RARs in addition to RXRs and this activation of RAR is why the non-responsive group (those with low triglyceride elevation) had decreased survival in the pivotal TARGRETIN® clinical trials.

At a dose of 400 mg/m$^2$/d, TARGRETIN® $C_{max}$ values in the blood are estimated to be around 8,000 nM, at which concentration there will be significant activation of RARs by TARGRETIN. Also, since the estimated TARGRETIN® $C_{max}$ values are around 2,000 nM at the lower dose (225 mg/m$^2$/d), some detrimental activation of RARs would occur even at this dose.

Accordingly, it is envisioned that a patient could be dosed with TARGRETIN® to determine the RAR activating threshold and the RXR effective dose for the patient; administering to the patient the RXR agonist at a level below the RAR activating threshold and at or above the RXR effective dose.

EXAMPLE 2

3,7-dimethyl-6(S),7(S)-methano,7-[1,1,4,4-tetramethyl-1,2,3,4-tetrah-ydronaphth-7-yl]2(E),4(E) heptadienoic acid (VTP 194204) is a highly potent ($EC_{50}$=0.1-0.5 nM) and specific RXR pan-agonist. VTP 194204 is believed to be readily used at purely RXR-activating doses.

Pre-Clinical Pharmacology

Figure 1A:
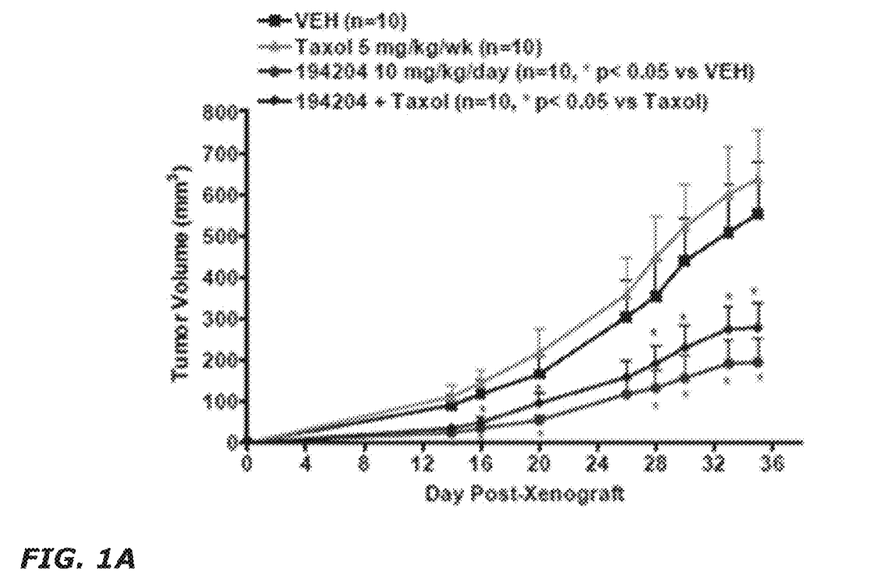
Figure 1B:
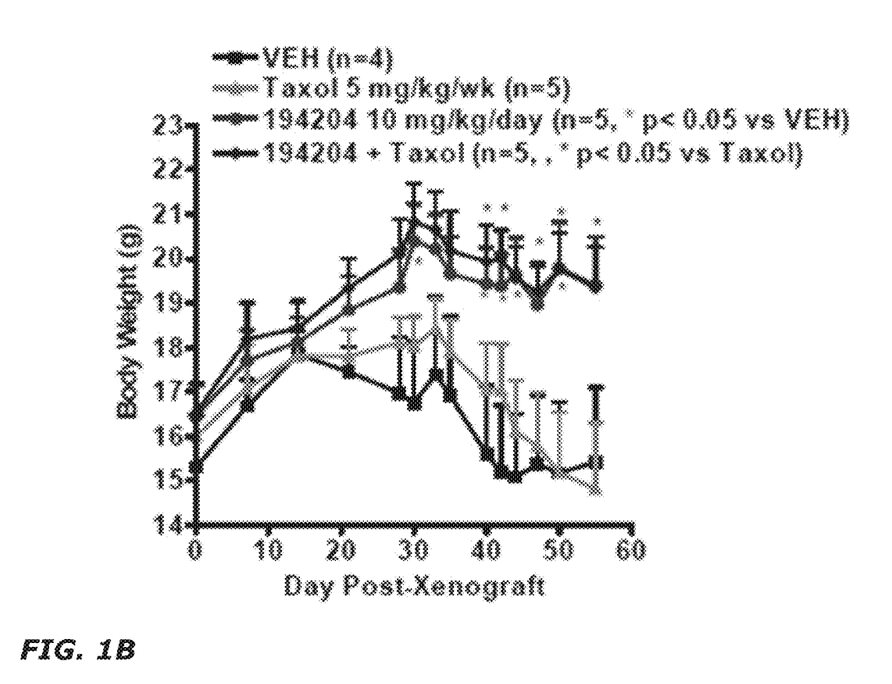
Figure 1C:
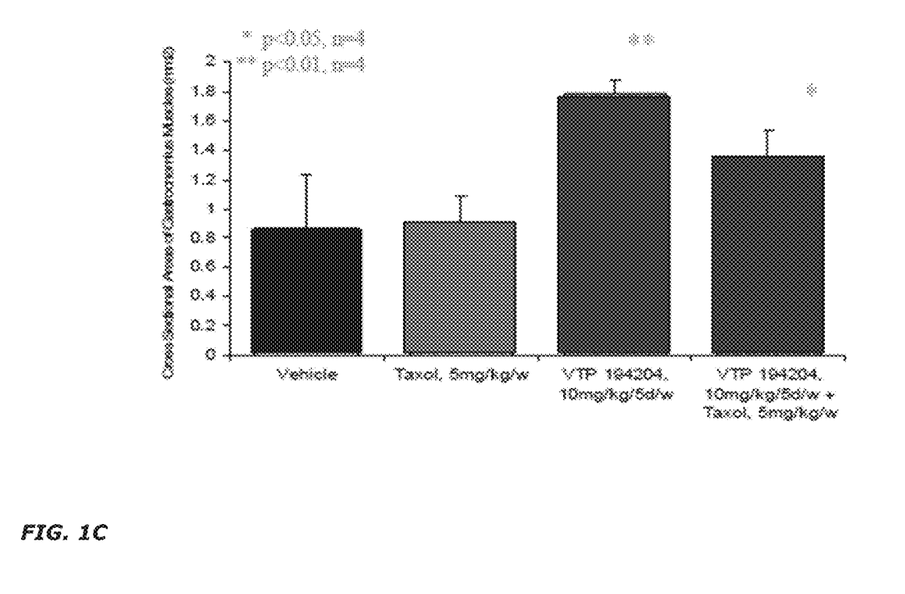
Figure 1D:
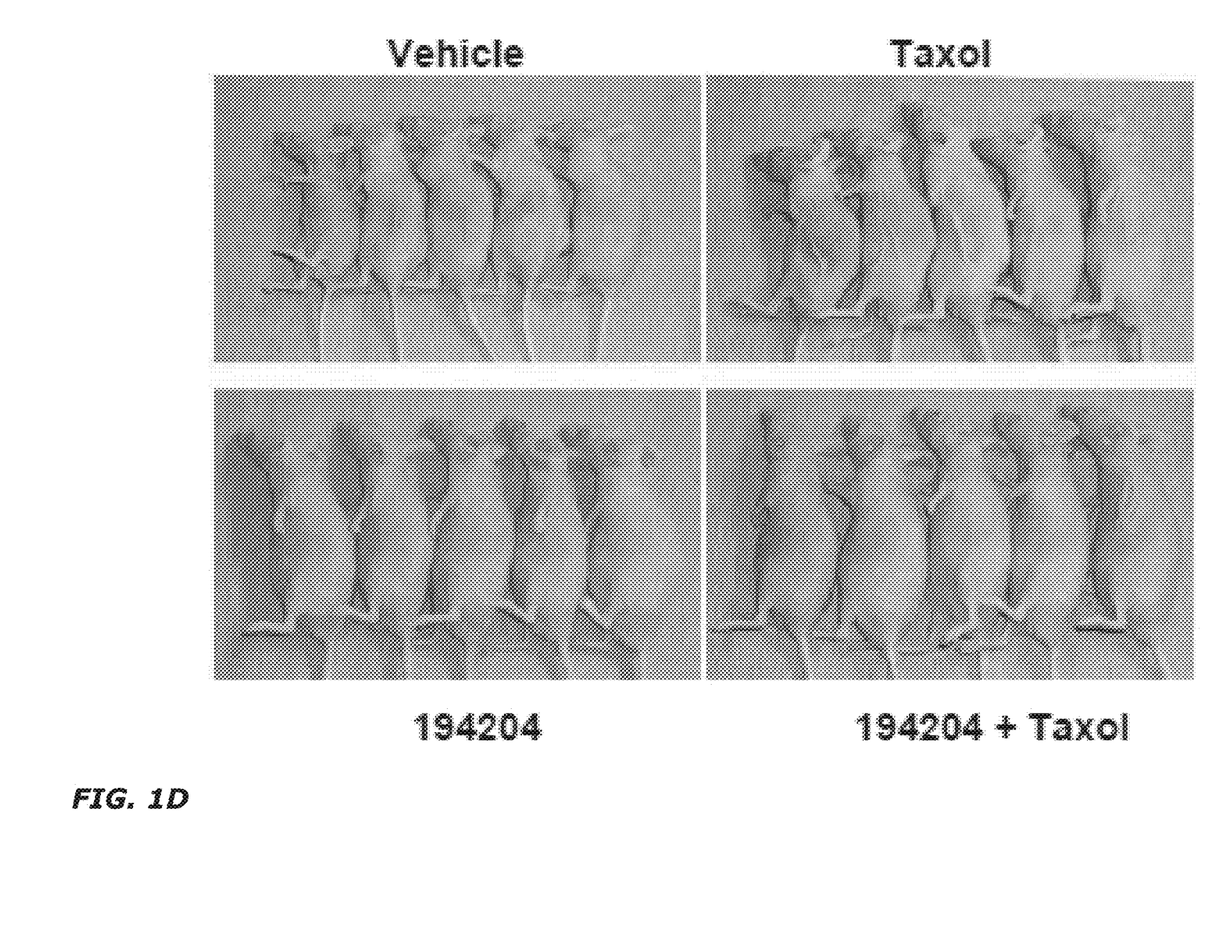

VTP 194204 exhibits tumor growth inhibitory effects in cell lines derived from a variety of tumor types and in animal models of breast and lung cancer. Also in models of cancer-induced cachexia, VTP 194204 maintained body weight, prevented loss of muscle and adipose tissue, improved food consumption, and prolonged survival. The anti-tumor and anti-cachectic properties of VTP 194204 are illustrated in FIG. 1. Preliminary studies indicate that the anti-cachectic properties of VTP 194204 are independent of its anti-tumor effects.

Pre-Clinical Safety

IND-enabling safety evaluation and toxicokinetic studies have been completed. No genotoxicity was observed in a battery of tests (Ames, mouse lymphoma TK, and rat micronucleus assays). Repeated oral dose studies for 4 weeks followed by recovery indicated the severe toxic doses of VTP 194204 to be greater than 200 mg/m$^2$/d and 60 mg/m$^2$/d in dogs and rats, respectively. These studies support a starting dose of 6 mg/m$^2$/d for the initial phase I-IIa dose escalation study.

Clinical Development Plan

The clinical plan will focus on achieving initial registration approval for treatment of NSCLC patients in a fourth-line setting. The initial Phase I-IIa study in NSCLC patients who have failed other therapies will be a dose-escalation study to determine a pharmacologically effective dose (full activation of RXRs as ascertained by pharmacodynamic markers) for VTP 194204. Preliminary survival data, in comparison to historical controls, will be obtained from the study.

The Phase II/III registration study in fourth-line NSCLC patients (n=~160) will compare VTP 194204 versus best supportive care with crossover upon disease progression. Approval will be based on a primary endpoint of progression-free survival. Subsequent or parallel studies will seek to expand clinical indications for VTP 194204 in NSCLC (e.g., combination with platinum-based therapies or Tarceva®), cancer-associated cachexia and breast cancer.

EXAMPLE 3

Prophetic Example

A Phase 1-2a Study of the Safety, Pharmacokinetics and Pharmacologically Effective Dose of Oral VTP 194204 in Patients with Advanced, Metastatic Refractory Non-Small Cell Lung Cancer (NSCLC)

Introduction

VTP 194204, a second-generation rexinoid, is a potent, specific full agonist at all three ($\alpha$, $\beta$ and $\gamma$) retinoid X receptors (RXRs). VTP 194204 exhibited tumor growth inhibitory effects in cell lines derived from a variety of tumor types and in animal models of breast and lung cancer. Also in models of cancer-induced cachexia, VTP 194204 maintained body weight, prevented loss of muscle and adipose tissue, improved food consumption, and prolonged survival. This Phase I-IIa clinical trial is designed to determine the safety, pharmacokinetics, and pharmacologically effective dose of VTP 194204 for the treatment of NSCLC patients through activation of RXRs.

Study Design
Study Endpoints
Primary:

To determine the safety of VTP 194204 administered orally on a daily schedule.

To determine the pharmacologically effective dose (PED) of VTP 194204 administered orally on a daily schedule.

To evaluate the pharmacokinetic profile of VTP 194204 in cancer patients.

Secondary:

To determine the effects of VTP 194204 on survival of NSCLC patients.

To determine anti-tumor activity of VTP 194204 as manifested by standard response criteria, or by tumor markers.

Patient Selection:

Number of Patients: Patients will be entered into the study in cohorts of 1 to 3. The total number of patients entered will be determined by the number of dose escalations Condition/Disease:

Patients will be those with NSCLC refractory to standard therapies.

Inclusion Criteria:

Histologically confirmed NSCLC refractory to conventional therapy.

Male or female, 18 to 75 years of age, inclusive.

ECOG Performance Status 0-2.

Life expectancy >8 weeks.

Hematology: Hemoglobin ≥8.5 g/dl
Platelets ≥100,000 cells/mm$^3$
Neutrophils ≥1500 cells/mm$^3$ PT and PTT within normal limits, except for patients receiving COUMADIN® (warfarin sodium, Bristol Myers Squibb) for thromboembolic prophylaxis only, in whom INR of less than 2 will be allowable.

Biochemistry: Total bilirubin 1.5×ULN
AST/ALT≤3.0×ULN
Serum creatinine ≤2.0 mg/dl
Serum calcium <11.5 mg/dl
Fasting serum triglycerides ≤2.5×ULN Endocrine: Thyroid stimulating hormone (TSH) WNL (>0.5 mU/L and <5.5 mU/L).

Negative urine pregnancy test for women of child-bearing potential at screening and on Day 0, and agreement to use two reliable forms of contraception during therapy and for 1 month following discontinuation of therapy unless abstinence is the chosen birth control method.

Exclusion Criteria:

Major surgery within previous 4 weeks; large field radiation therapy (>25% of the patient's total marrow) or chemotherapy (including investigational agents or participation in another clinical study) within previous 4 weeks; mitomycin C or nitrosoureas within 6 weeks.

Systemic retinoid therapy, or vitamin A at dosages >5,000 IU per day, during previous 4 weeks.

Patients with any prior or current history of thyroid disease, with any history of pituitary disease, or with any history of prior or current treatment with thyroid replacement hormone.

Primary brain tumors, active brain metastasis including progression from last scan or evidence of cerebral edema, or clinical symptoms of brain metastasis. Patients with prior history of brain metastasis must have brain imaging (e.g., CT, MRI) performed.

Requirement for steroids or anticonvulsant medication. (Patients taking stable dosages of GnRH analogues or MEGACE® (megestrol acetate, Bristol Myers Squibb) for at least the previous 3 months will be allowed into the study).

Current enrollment in an investigational drug or device study or participation in such a study within 30 days of entry into this study.

Known HIV-positive patients.

Females who are pregnant, nursing, or planning a pregnancy.

History of gastrointestinal disorders (medical disorders or extensive surgery) which may interfere with absorption of study medication.

Clinically significant abnormalities on screening ECG.

Treatment
Definitions

PED: defined as the dose at which 90% of all TSH measurements in all patients in a 4-week cycle were 90% below the corresponding basal TSH values provided that at 50% of this dose at least 75% of all TSH measurements in all patients in a 4-week cycle were 80% below the corresponding basal TSH values. It is expected that effective activation of RXRs will occur at a PED.

DLT: defined as one of the following toxicities (all toxicities graded according to the NCI Common Toxicity Criteria, version 2.0 except the RAR biomarkers):

(1) More than 2-fold increase in levels of at least one RAR biomarker (e.g., CYP 26A, CD38).

(2) Any symptomatic Grade 2 toxicity that requires hold or reduction of study drug administration.

(3) Any Grade 3 or higher symptomatic toxicity (excluding nausea/vomiting in the absence of optimal anti-emetics).

(4) Any Grade 3 asymptomatic biochemical (except SGOT (AST) or SGPT (ALT)) or hematologic toxicity persisting >7 days.

(5) SGOT (AST)/SGPT (ALT)>10×ULN (upper limit of normal range).

(6) Any Grade 4 biochemical or hematologic toxicity.

MTD: defined as the highest dose level at which less than 2 of a cohort of patients experience a dose-limiting toxicity (DLT) during a minimum period of 4 weeks. This means for a dose to meet the definition of MTD, the study drug will have been administered at that dose to a cohort of at least three patients for at least 4 weeks and only one patient will have experienced only one DLT during that time interval. This will generally be one dose level below that at which DLT occurs in 2 patients. There is no specified minimum duration of study drug exposure required for consideration of a case of DLT for the determination of the MTD.

The derivation of a recommended dose for future studies will incorporate tolerability of the drug over 8 weeks in at least 3 patients. Thus, if the proposed recommended dose has fewer than 3 patients treated for at least 8 weeks, additional patients will be enrolled at that dose level.

Duration:

A treatment cycle will be 4 weeks of daily oral study drug administration (Cycle 1) in the absence of dose-limiting toxicity (DLT). After 4 weeks, patients may be allowed to continue on study in 4-week increments of daily oral study drug administration at the same dose level (or reduced dose level) if further treatment is judged to be of possible clinical benefit (Cycles 2-12) to a maximum of 12 cycles.

Dosage/Dose Regimen:

Three patients will be accrued at each dose level. The initial daily dose of VTP 194204 will be approximately 0.2 mg/m$^2$/day taken as a single, oral dose. Doses will be escalated as described below. In the absence of toxicity greater than Grade 2 on the NCI toxicity scale over a period of 4 weeks, the dose will be escalated by 100% for one to three patients in each subsequent cohort. No intra-patient dose escalation will be allowed from one cycle to the next. After a given cycle, patients may be allowed to continue on study in further increments of four weeks at the same dose as in the previous cycle, if the investigator determines it to be in the patient's interests to continue in the study. The initial dose and all subsequent dose escalations will be to the nearest capsule size.

Thyroid hormone and thyroid stimulating hormone (TSH) levels, biomarkers of RXR activation, will be measured weekly in all patients during Cycle 1. In addition, levels of potential biomarkers for retinoic acid receptor (RAR)-specific activity such as retinoic acid-inducible cytochrome P450 enzyme (CYP26A), cellular retinol binding protein-I (CRBPI), CD38, and RAR γ2 will be simultaneously monitored in blood cells at the messenger RNA level by quantitative PCR assays. At a given dose level, if 75% or greater of all TSH measurements in all patients in a 4-week cycle are 80% below the corresponding basal TSH values and no patient exhibits toxicity greater than Grade 2, then a further dose escalation of 100% will be made in a new cohort of 3 additional patients. If 90% of all TSH measurements in all patients in a 4-week cycle at this new dose are 90% below the corresponding basal TSH values, then a pharmacologically effective dose (PED) will be deemed to have been reached. If not, further dose escalations of 100% (or of lesser amounts) will be made in new cohorts of 3 patients each until a PED as defined above is reached unless a dose limiting toxicity (DLT) is reached earlier. The DLT is defined as equal or greater than 2-fold increase in a RAR biomarker level and/or Grade 3 toxicity whichever is reached first. If a PED is reached prior to a DLT, 6 more patients will be enrolled at the PED in order to further validate the PED.

If a patient develops a DLT, 3 additional patients will be enrolled at that dose level. If none of the 3 additional patients develops a DLT over a period of 4 weeks, the dosage will continue to be escalated 100% for one to three patients in the subsequent cohorts. However, if 1, 2, or all 3 additional patients develop DLT, the dosage will be escalated by 50% in a new cohort of 3 patients. Dose escalation will be carried out until a dose equivalent to PED is reached, unless a dose limiting toxicity (DLT) is reached earlier.

If one of the patients entered at a dose level experiences DLT, up to 3 additional patients will be entered at that dose level. If none of the 3 additional patients experiences a DLT, dose escalation will proceed with a dose increment of 33% in at least 3 patients per dose level. However, if a second patient in the cohort experiences DLT, then the maximum tolerated dose (MTD) will be deemed to be exceeded. Dose reduction due to DLT or intolerability will be 50% unless a 50% dose reduction will result in dosing at a previously investigated level, then a 33% dose reduction will be investigated.

Visit Schedule:

Patients will be seen for assessment every 7 days (+/−1 day) for 28 days. Thus, there will be 6 scheduled visits (including screening visit) to the end of the first cycle. Those patients who continue on treatment after 28 days will be seen every 14 days (+/−2 days), or more frequently if clinically required.

Prophetic Results

The following are predicted, not actual, results:

PED is 1 mg/m$^2$/d. The blood concentration of VTP 194204 at the PED is 3±1 ng/mL. There was no discernible increase of levels of RAR biomarkers at any of the VTP 194204 dosages including the PED. Thus, dosages of VTP 194204 of approximately 1 mg/m$^2$/day are considered to be purely RXR-activating dosages (i.e., no RAR activation). Such dosages are optimal for treating NSCLC patients. The average median survival for the NSCLC patients in this study was 8.5 months compared to approximately 4 months for historical, matched control patients.

EXAMPLE 4

Prophetic Example

A Randomized Phase III Trial Comparing VTP 194204/Carboplatin/Paclitaxel versus Carboplatin/Paclitaxel in Chemotherapy-Naive Patients with Advanced or Metastatic Non-Small Cell Lung Cancer (NSCLC)

Introduction

VTP 194204, a second-generation rexinoid, is a potent, specific full agonist at all three retinoid X receptors. VTP 194204 exhibited tumor growth inhibitory effects in cell lines derived from a variety of tumor types and in animal models of breast and lung cancer. Also in models of cancer-induced cachexia, VTP 194204 maintained body weight, prevented loss of muscle and adipose tissue, improved food consumption, and prolonged survival. A Phase III trial is designed to demonstrate the survival benefit of the addition of VTP 194204 to carboplatin/paclitaxel chemotherapy.

Study Design:

Patient Selection

Patients are selected to meet all following conditions

NSCLC at Stage IIIB with pleural effusion or Stage IV;

No prior chemotherapy;

ECOG=0, 1.

Treatment:

Patients stratified by disease stage and gender are randomized to receive VTP 194204 once daily at a pure RXR-activating dose and carboplatin AUC 6 and paclitaxel 200 mg/m², i.e., every 3 weeks or carboplatin/paclitaxel alone. The pure RXR activation dose of VTP 194204 is determined by monitoring induction of hypothyroidism (reduction in TSH levels), a pharmacological biomarker for RXR activation, in the absence of induction of RAR biomarkers in blood.

Study Endpoints:
Primary endpoint: Overall survival
Secondary endpoint: Kaplan-Meier projected two-year survival rates.
Prophetic Results:
The predicted, not actual, clinical results are presented in TABLE 2:

TABLE 2

| PROPHETIC, NOT ACTUAL, RESULTS | | |
|---|---|---|
| Treatment Group | Median Survival (Months) | Two-Year Survival Rates (%) |
| Carboplatin/Paclitaxel | 9.2 | 16 |
| VTP 194204/Carboplatin/Paclitaxel | 15 | 30 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto. All publications, patents and patent applications mentioned in this specification are herein incorporated by reference to the same extent as if each individual publication or patent application were specifically and individually designated as having been incorporated by reference.

What is claimed is:

1. A method of treating pancreatic cancer, the method comprising administering to a patient in need of such treatment a retinoid X receptor (RXR) agonist at a dose which does not activate retinoic acid receptors (RAR) and wherein the dose of the RXR agonist is from about 1 to about 20 mg/m²/day, wherein the RXR agonist has a chemical structure or a pharmaceutically acceptable salt thereof.

2. The method according to claim 1, wherein the dose is determined by dosing the patient with increasing concentrations of a RXR agonist until an RXR effective dose is reached which does not activate RAR.

3. The method according to claim 2, wherein the RXR effective dose is determined by measuring reduction of a patient's TSH levels or at least one RAR biomarker expressed by the patient.

4. The method according to claim 3, wherein the RAR biomarker is selected from the group consisting of CYP26 level, CRBPI level and combinations thereof.

5. The method according to claim 1, further comprising measuring the patient's $C_{max}$ of the RXR agonist, and adjusting the dose to maintain the patient's $C_{max}$, at an optimal level.

6. The method according to claim 1, further comprising treating the patient with at least one other agent selected from the group consisting of anti-cancer agents, triglyceride lowering agents and TSH modulating agents.

7. The method according to claim 6, wherein the anti-cancer agent is selected from the group consisting of a platinum-based compound, a cytotoxic drug, and mixtures thereof.

8. The method according to claim 1, wherein the dose of the RXR agonist is from about 1 to about 10 mg/m²/day.

9. The method according to claim 1, wherein the dose of the RXR agonist is from about 10 to about 20 mg/m²/day.

10. The method according to claim 1, wherein the RXR agonist is 3,7-dimethyl-6(S),7(S)-methano,7-[1,1,4,4-tetramethyl-1,2,3,4-tetrahydronaphth-7- yl](E),4(E) heptadienoic acid.

* * * * *